(12) United States Patent
Sugiyama et al.

(10) Patent No.: US 9,279,890 B2
(45) Date of Patent: *Mar. 8, 2016

(54) RADIATION IMAGE ACQUISITION DEVICE

(75) Inventors: Mototsugu Sugiyama, Hamamatsu (JP); Toshiyasu Suyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 245 days.

This patent is subject to a terminal disclaimer.

(21) Appl. No.: 13/981,469

(22) PCT Filed: Oct. 21, 2011

(86) PCT No.: PCT/JP2011/074327
§ 371 (c)(1),
(2), (4) Date: Oct. 1, 2013

(87) PCT Pub. No.: WO2012/101879
PCT Pub. Date: Aug. 2, 2012

(65) Prior Publication Data
US 2014/0016753 A1    Jan. 16, 2014

(30) Foreign Application Priority Data
Jan. 25, 2011    (JP) .................... 2011-013192

(51) Int. Cl.
*G01N 23/04*    (2006.01)
*G01T 1/20*    (2006.01)

(52) U.S. Cl.
CPC ............ *G01T 1/2002* (2013.01); *G01N 23/04* (2013.01); *G01T 1/20* (2013.01); *G01N 2223/611* (2013.01)

(58) Field of Classification Search
CPC ..... G01N 23/223; G01N 23/06; G01N 23/18; G01N 23/043; G01N 23/04; A61B 6/485; A61B 6/482; A61B 6/4225; H04N 5/32

USPC .................... 378/44, 51, 58, 62, 98.3, 98.9
See application file for complete search history.

(56) References Cited

U.S. PATENT DOCUMENTS

| | | | |
|---|---|---|---|
| 4,578,803 A | 3/1986 | Macovski | |
| 5,864,146 A | 1/1999 | Karellas | |
| 7,405,406 B1 | 7/2008 | Nagarkar et al. | |

FOREIGN PATENT DOCUMENTS

| | | |
|---|---|---|
| JP | S63-079043 | 4/1988 |
| JP | H5-152391 | 6/1993 |

(Continued)

OTHER PUBLICATIONS

U.S. Appl. No. 13/981,372, Mototsugu Sugiyama et al.
(Continued)

*Primary Examiner* — Jurie Yun
(74) *Attorney, Agent, or Firm* — Drinker Biddle & Reath LLP (57) ABSTRACT

A radiation image acquisition device includes: a radiation source which emits radiation; a wavelength conversion member of a flat plate shape which generates scintillation light according to incidence of the radiation emitted from the radiation source and transmitted by an object; first imaging means which condenses and images the scintillation light emitted from an entrance surface for the radiation in the wavelength conversion member in a direction of a normal to the entrance surface; and second imaging means which condenses and images the scintillation light emitted from a surface opposite to the entrance surface in the wavelength conversion member in a direction of a normal to the opposite surface.

21 Claims, 8 Drawing Sheets

(56) References Cited

FOREIGN PATENT DOCUMENTS

| | | |
|---|---|---|
| JP | H5-312734 | 11/1993 |
| JP | 7-27866 A | 1/1995 |
| JP | H8-061941 | 3/1996 |
| JP | 2000-510729 A | 8/2000 |
| JP | 2000-298198 A | 10/2000 |
| JP | 2001-004561 | 1/2001 |
| JP | 2005-207827 A | 8/2005 |
| JP | 2007-155653 A | 6/2007 |
| JP | 2007-327967 | 12/2007 |
| JP | 2008-164429 | 7/2008 |

OTHER PUBLICATIONS

U.S. Appl. No. 13/981,490, Mototsugu Sugiyama et al.
U.S. Office Action dated May 19, 2015 that issued in U.S. Appl. No. 13/981,490 including Double Patenting Rejections on pp. 2-4.
U.S. Office Action dated May 19, 2015 that issued in U.S. Appl. No. 13/981,372 including Double Patenting Rejections on pp. 2-5.

RADIATION IMAGE ACQUISITION DEVICE

TECHNICAL FIELD

The present invention relates to a radiation image acquisition device.

BACKGROUND ART

There is the conventionally known apparatus for applying X-rays emitted from an X-ray source and transmitted by an imaging object, onto a scintillator of a flat plate shape, detecting visible light (scintillation light) generated in the scintillator, by solid-state photodetectors laid on both surfaces of the scintillator, and superimposing image signals from the respective solid-state photodetectors on each other to acquire a radiation image, as described in Patent Literature 1 below. In this apparatus, the photodetector elements are coupled to the X-ray entrance surface and to the back surface behind it in the scintillator and the visible light is detected by each of the entrance-surface-side photodetector element and the back-surface-side photodetector element, thereby increasing efficiency of detection of the visible light.

CITATION LIST

Patent Literature

Patent Literature 1: Japanese Patent Application Laid-open No. H07-27866

SUMMARY OF INVENTION

Technical Problem

The apparatus for detecting the scintillation light on the both surfaces of the scintillator as described above can acquire radiation images in different energy bands on the entrance surface side and on the back surface side behind it, so as to enable acquisition of so-called dual-energy images In the foregoing conventional apparatus, however, the radiation transmitted by the object passes through the entrance-surface-side photodetector element to reach the scintillator, and for this reason, radiation in a relatively low energy band is absorbed by the entrance-surface-side photodetector element. For example, when the object is formed of a lightweight atom, the radiation transmitted by the object can be absorbed by the entrance-surface-side photodetector element. As described above, the conventional apparatus has the problem that the radiation transmitted by the object is affected by the entrance-surface-side photodetector element.

It is therefore an object of the present invention to provide a radiation image acquisition device capable of acquiring radiation images in different energy bands while reducing the influence on the radiation transmitted by the object.

Solution to Problem

A radiation image acquisition device according to one aspect of the present invention includes: a radiation source which emits radiation; a wavelength conversion member of a flat plate shape which generates scintillation light according to incidence of the radiation emitted from the radiation source and transmitted by an object; first imaging means which condenses and images the scintillation light emitted from an entrance surface for the radiation in the wavelength conversion member in a direction of a normal to the entrance surface; and second imaging means which condenses and images the scintillation light emitted from a surface opposite to the entrance surface in the wavelength conversion member in a direction of a normal to the opposite surface.

In the radiation image acquisition device according to the one aspect of the present invention, the first imaging means and the second imaging means condense and image the respective scintillation light beams emitted from the entrance surface for the radiation and the opposite surface behind it in the wavelength conversion member. This realizes dual-energy imaging to acquire radiation images in different energy bands. In this connection, the first imaging means is arranged at a position apart from the wavelength conversion member, in order to condense the scintillation light emitted from the entrance surface. Therefore, the radiation image acquisition device can have the configuration wherein no imaging means is interposed between the object and the wavelength conversion member, thereby avoiding an incident such that the imaging means affects the radiation transmitted by the object. Accordingly, it is feasible to reduce the influence on the radiation transmitted by the object. Furthermore, since the first imaging means and the second imaging means condense the scintillation light beams emitted from the entrance surface and from the opposite surface behind it in the directions of the respective normals thereto, they both can acquire radiation images with no perspective, which facilitates an operation between the images on the entrance surface side and on the opposite surface side.

The radiation image acquisition device may be configured in a mode such that each of the first imaging means and the second imaging means has: a condensing lens unit for condensing the scintillation light emitted from the wavelength conversion member; and an imaging unit for imaging the scintillation light thus condensed. In this case, the scintillation light is condensed with focus on each of the entrance surface and the opposite surface of the wavelength conversion member, which enables acquisition of bright radiation images with good energy separation.

The radiation image acquisition device may be configured in a mode such that the radiation source is arranged so that an angle between an optical axis of the radiation source and the entrance surface is larger than 0° and smaller than 90°, and that the first imaging means is arranged on the normal to the entrance surface. In this case, the first imaging means can directly condense the scintillation light in the direction of the normal to the entrance surface, and the first imaging means can be arranged off the optical axis of the radiation source. Therefore, the aforementioned operational effect can be readily achieved and the first imaging means can be prevented from being exposed to the radiation, which can suppress generation of noise inside the first imaging means.

The radiation image acquisition device may be configured in a mode such that the radiation source is arranged on the normal to the entrance surface and that the first imaging means is arranged at a position off the normal to the entrance surface so as to condense the scintillation light via a reflecting mirror arranged between the wavelength conversion member and the radiation source. In this case, since the radiation source is arranged on the normal to the entrance surface, no perspective is made in a projection image on the wavelength conversion member, which eliminates a need for an operation to correct for a perspective of the projection image. Furthermore, the first imaging means can be prevented from being exposed to the radiation, which can suppress generation of noise inside the first imaging means.

The radiation image acquisition device may be configured in a mode such that the second imaging means is arranged at a position off the normal to the opposite surface so as to condense the scintillation light via a reflecting mirror arranged on the normal to the opposite surface. In this case, the second imaging means can be prevented from being exposed to the radiation, which can suppress generation of noise inside the second imaging means. Furthermore, this configuration permits adjustment of optical path lengths from the wavelength conversion member to the first and second imaging means, which facilitates position alignment of the first and second imaging means. As a consequence of this, it becomes easier to match imaging conditions of the first and second imaging means (e.g., simultaneity of imaging times and identity of imaging positions).

The radiation image acquisition device may be configured in a mode such that a tapered fiber is arranged between the opposite surface of the wavelength conversion member and the second imaging means so as to face the opposite surface. In this case, the tapered fiber can condense the scintillation light on the opposite surface side at a high light condensing efficiency. Furthermore, the tapered fiber blocks the radiation whereby the second imaging means can be prevented from being exposed to the radiation.

The radiation image acquisition device may be configured in a mode such that the object is a semiconductor device and that the radiation image acquisition device is applied to a semiconductor failure inspection device an inspection target of which is the semiconductor device. In this case, since the radiation transmitted by the semiconductor device as the inspection target is not cut by the imaging unit (imaging device for acquisition of image), the inspection device can detect a failure or the like of the semiconductor device with high accuracy.

Advantageous Effect of Invention

The one aspect of the present invention enables the acquisition of radiation detection images in different energy bands and the reduction of the influence on the radiation transmitted by the object.

BRIEF DESCRIPTION OF DRAWINGS

FIGS. 7(a) and (b) is front views of the radiation image acquisition devices which are modification examples of the present invention.

DESCRIPTION OF EMBODIMENTS

Embodiments of the present invention will be described below in detail with reference to the drawings. Identical or equivalent portions will be denoted by the same reference signs in the description of the drawings, without redundant description. It is noted that each drawing is prepared by way of illustration only and is depicted so as to emphasize each part as object of description in particular. For this reason, the dimensional ratios of respective members in the drawings are not always coincident with actual ones.

Figure 1:
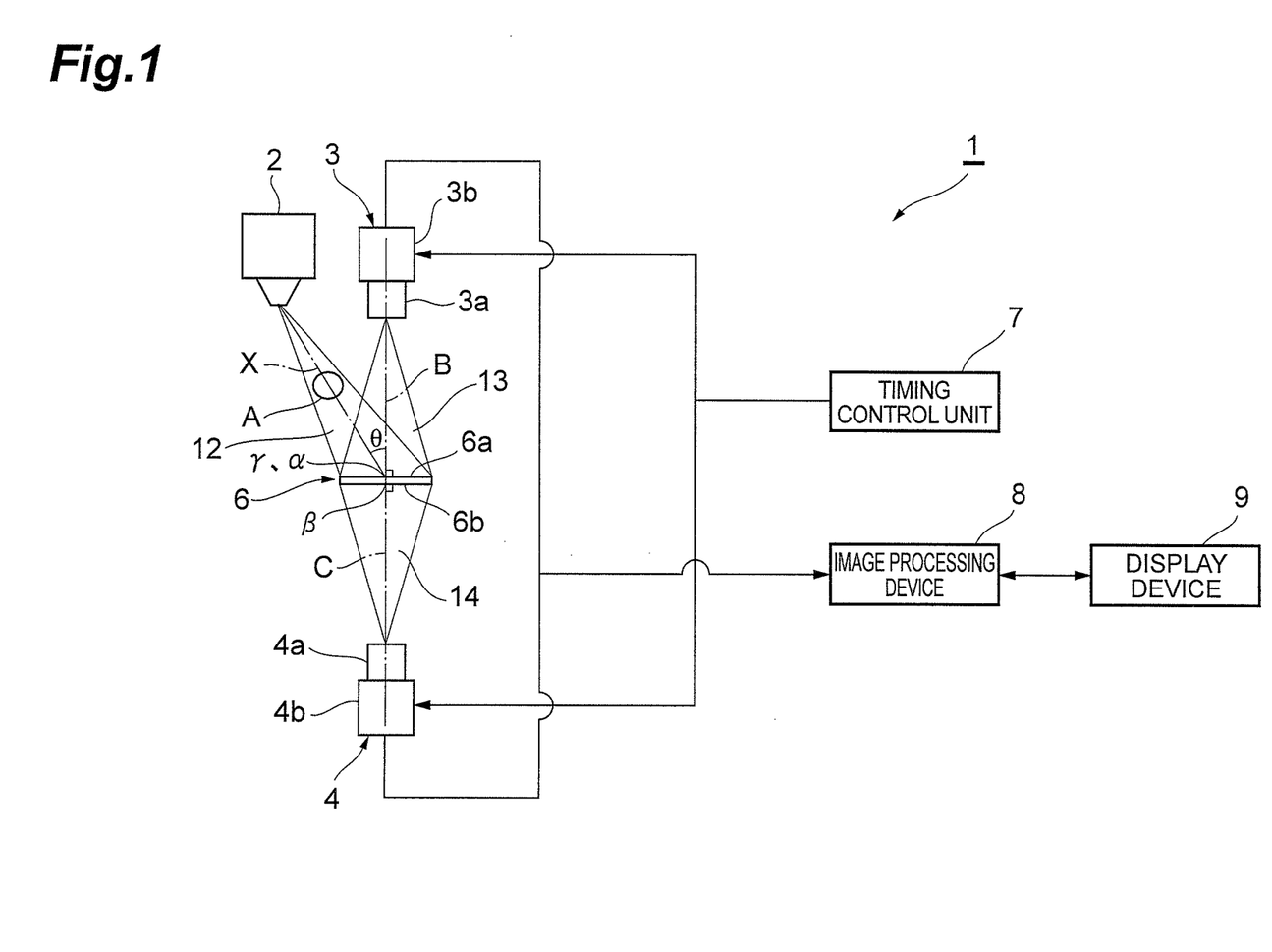
FIG. 1 is a front view of the radiation image acquisition device according to the first embodiment of the present invention.

As shown in FIG. 1, the radiation image acquisition device 1 is a device for acquiring a radiation image of an object A, e.g., an electronic component such as a semiconductor device, or a foodstuff. The radiation image acquisition device 1 is provided with a radiation source 2 which emits radiation such as white X-rays toward the object A, a wavelength conversion plate 6 which generates scintillation light according to incidence of the radiation transmitted by the object A after emitted from the radiation source 2, a front observation photodetector 3 which condenses and images the scintillation light emitted from an entrance surface 6a for the radiation in the wavelength conversion plate 6, and a back observation photodetector 4 which condenses and images the scintillation light emitted from a back surface 6b being a surface opposite to the entrance surface 6a. These radiation source 2, wavelength conversion plate 6, front observation photodetector 3, and back observation photodetector 4 are housed in a housing not shown and fixed in the housing.

The wavelength conversion plate 6 is a wavelength conversion member of a flat plate shape, e.g., a scintillator of any one of $Gd_2O_2S:Tb$, $Gd_2O_2S:Pr$, $CsI:Tl$, $CdWO_4$, $CaWO_4$, $Gd_2SiO_5:Ce$, $Lu_{0.4}Gd_{1.6}SiO_5$, $Bi_4Ge_3O_{12}$, $Lu_2SiO_5:Ce$, $Y_2SiO_5$, $YAlO_3:Ce$, $Y_2O_2S:Tb$, $YTaO_4:Tm$, and so on. The thickness of the wavelength conversion plate 6 is set to an appropriate value depending upon a radiation energy band detected, in the range of several 1 μm to several mm.

The front observation photodetector 3 (which will be referred to hereinafter as "front detector 3") is an imaging means of an indirect conversion method that photographs a projection image (radiation transmission image) of the object A projected on the wavelength conversion plate 6, from the entrance surface 6a side of the wavelength conversion plate 6. The front detector 3 is a detector of a lens coupling type having a condensing lens unit 3a for condensing the scintillation light emitted from the entrance surface 6a of the wavelength conversion plate 6, and an imaging unit 3b for imaging the scintillation light condensed by the condensing lens unit 3a. The condensing lens unit 3a condenses the scintillation light in a front detector field 13. The imaging unit 3b to be used herein is, for example, a CMOS sensor, a CCD sensor, or the like. A light receiving surface of the imaging unit 3b can be arranged approximately parallel to the entrance surface 6a.

The back observation photodetector 4 (which will be referred to hereinafter as "back detector 4") is an imaging means of the indirect conversion method that photographs a projection image (radiation transmission image) of the object A projected on the wavelength conversion plate 6, from the back surface 6b side of the wavelength conversion plate 6. The back detector 4 is a detector of the lens coupling type having a condensing lens unit 4a for condensing the scintillation light emitted from the back surface 6b of the wavelength conversion plate 6, and an imaging unit 4b for imaging the scintillation light condensed by the condensing lens unit 4a, and thus it has the same configuration as the aforementioned front detector 3. The condensing lens unit 4a condenses the scintillation light in a back detector field 14. The imaging unit 4b to be used herein is, for example, a CMOS sensor, a CCD sensor, or the like. A light receiving surface of the imaging unit 4b can be arranged approximately parallel to the back surface 6b.

Furthermore, the radiation image acquisition device 1 is provided with a timing control unit 7 for controlling imaging timing at the front detector 3 and at the back detector 4, an image processing device 8 for receiving input image signals from the front detector 3 and from the back detector 4 and executing a predetermined processing procedure such as image processing based on each of the input image signals, and a display device 9 for receiving an input image signal from the image processing device 18 and displaying a radiation image. The timing control unit 7 and the image processing device 8 are composed of a computer having a CPU (Central Processing Unit), a ROM (Read Only Memory), a RAM (Random Access Memory), input/output interfaces, and so on. The display device 9 to be used herein is a well-known display. The timing control unit 7 and the image processing device 8 may be configured as a program executed by a single computer or as respective units provided individually.

The below will describe the positional relationship among the aforementioned radiation source 2, wavelength conversion plate 6, front detector 3, and back detector 4. As shown in FIG. 1, the radiation source 2 is arranged so that an optical axis X of the radiation makes a predetermined angle θ with respect to a normal B to the entrance surface 6a of the wavelength conversion plate 6. Namely, the radiation source 2 faces the object A and the entrance surface 6a and is arranged at a position off the normal B to the entrance surface 6a. In other words, the radiation source 2 is arranged so that the angle between the optical axis X and the entrance surface 6a is larger than 0° and smaller than 90°. The optical axis X of the radiation here is a straight line connecting a radiation emission point of the radiation source 2 and an arbitrary point γ on the entrance surface 6a of the wavelength conversion plate 6. In the present embodiment, the arbitrary point γ is set to be a central point of the entrance surface 6a and in this case, the radiation is radiated with little relative unevenness. The normal B here is a straight line extending normally to the entrance surface 6a from an arbitrary point α on the entrance surface 6a. In the present embodiment, the arbitrary point α is set to be the central point of the entrance surface 6a and thus the optical axis X of the radiation and the normal B intersect at the arbitrary point γ (arbitrary point α) on the entrance surface 6a. It is a matter of course that the arbitrary point γ and the arbitrary point α do not have to be coincident with the central point of the entrance surface 6a and do not have to be the same point, either.

The front detector 3 is arranged so that an optical axis of the incorporated condensing lens unit 3a is perpendicular to the entrance surface 6a, so as to be able to image the scintillation light emitted from the entrance surface 6a of the wavelength conversion plate 6. In this configuration, the optical axis of the condensing lens unit 3a is coincident with the normal B to the entrance surface 6a. Namely, the front detector 3 faces the entrance surface 6a and is arranged on the normal B to the entrance surface 6a. Therefore, the front detector 3 can image the scintillation light emitted in the direction of the normal B to the entrance surface 6a and thus readily acquire an image without a significant perspective. The condensing lens unit 3a focuses on the entrance surface 6a and condenses the scintillation light emitted in the direction of the normal B from the entrance surface 6a, toward the imaging unit 3b.

As described above, the front detector 3 is arranged off the optical axis X of the radiation source 2. Namely, the front detector 3 is arranged so as to be located apart from an emission region of the radiation from the radiation source 2 (which is a region where a radiation beam 12 exists). This arrangement prevents the front detector 3 from being exposed to the radiation from the radiation source 2 and prevents a direct conversion signal of radiation from being produced inside the front detector 3 to generate noise. Furthermore, the front detector 3 is arranged so that a perpendicular to the entrance surface 6a of the wavelength conversion plate 6 from the center of the condensing lens unit 3a is within the range of the entrance surface 6a and so that it is located above the entrance surface 6a of the wavelength conversion plate 6. This configuration allows the front detector 3 to detect a relatively large quantity of scintillation light.

The back detector 4 is arranged so that an optical axis of the incorporated condensing lens unit 4a is perpendicular to the back surface 6b, so as to be able to image the scintillation light emitted from the back surface 6b of the wavelength conversion plate 6. In this configuration, the optical axis of the condensing lens unit 4a is coincident with a normal C to the back surface 6b. Namely, the back detector 4 faces the back surface 6b and is arranged on the normal C to the back surface 6b. Therefore, the back detector 4 can image the scintillation light emitted in the direction of the normal C to the back surface 6b and thus readily acquire an image without a significant perspective. The normal C here is a straight line extending normally to the back surface 6b from an arbitrary point β on the back surface 6b. Particularly, in the present embodiment, the arbitrary point β is set at a central point of the back surface 6b, the arbitrary point α on the entrance surface 6a and the arbitrary point β on the back surface 6b are located on the same straight line, and this straight line is coincident with the normal B and the normal C. The condensing lens unit 4a focuses on the back surface 6b and condenses the scintillation light emitted in the direction of the normal C from the back surface 6b, toward the imaging unit 4b.

In the radiation image acquisition device 1, an optical path length from the entrance surface 6a of the wavelength conversion plate 6 to the front detector 3 is equal to an optical path length from the back surface 6b of the wavelength conversion plate 6 to the back detector 4. The optical path length from the entrance surface 6a of the wavelength conversion plate 6 to the front detector 3 may be different from the optical path length from the back surface 6b of the wavelength conversion plate 6 to the back detector 4, but in this case, the sizes of the images need to be matched by image processing or the like.

The following will describe the operation of the radiation image acquisition device 1 having the above-described configuration. First, the timing control unit 7 performs control to make the front detector 3 and the back detector 4 simultaneously carry out their respective imaging operations. The imaging of radiation transmission images of the object A in different energy bands can be implemented based on the imaging timing control by the timing control unit 7. In more detail, the front detector 3 acquires the radiation transmission image in a relatively low energy band and the back detector 4 the radiation transmission image in a relatively high energy band. This operation realizes dual-energy imaging. It is noted that the radiation image acquisition device 1 is configured to allow control to make the imaging times of the front detector 3 and the back detector 4 different from each other. The device may also be configured to control the front detector 3 and the back detector 4 to different exposure times and/or different numbers of photos taken thereby.

The functions of the front detector 3 and the back detector 4 will be specifically described in more detail. The front detector 3 detects fluorescence (scintillation light) resulting from conversion on the side relatively near the entrance surface 6a. The detection of the fluorescence resulting from the conversion on the entrance surface 6a side is characterized by little blurring of fluorescence and high luminance of fluorescence. This is because the front observation can be less affected by diffusion and self-absorption inside the wavelength conversion plate 6. On the other hand, the back detector 4 detects fluorescence resulting from conversion on the side relatively near the back surface 6b of the wavelength conversion plate 6. In this case as well, the observation can be less affected by diffusion and self-absorption inside the wavelength conversion plate 6.

Next, the front detector 3 and the back detector 4 output their respective image signals corresponding to the radiation images on both of the front and back surfaces, to the image processing device 8. When the image processing device 8 receives the respective input image signals from the front detector 3 and from the back detector 4, the image processing device 8 executes the predetermined processing such as an inter-image operation, e.g., a differential operation or an addition operation, based on the input image signals, and outputs an image signal after the image processing to the display device 9. When the display device 9 receives the input image signal after the image processing from the image processing device 8, the display device 9 displays a radiation image according to the input image signal after the image processing.

Figure 2:
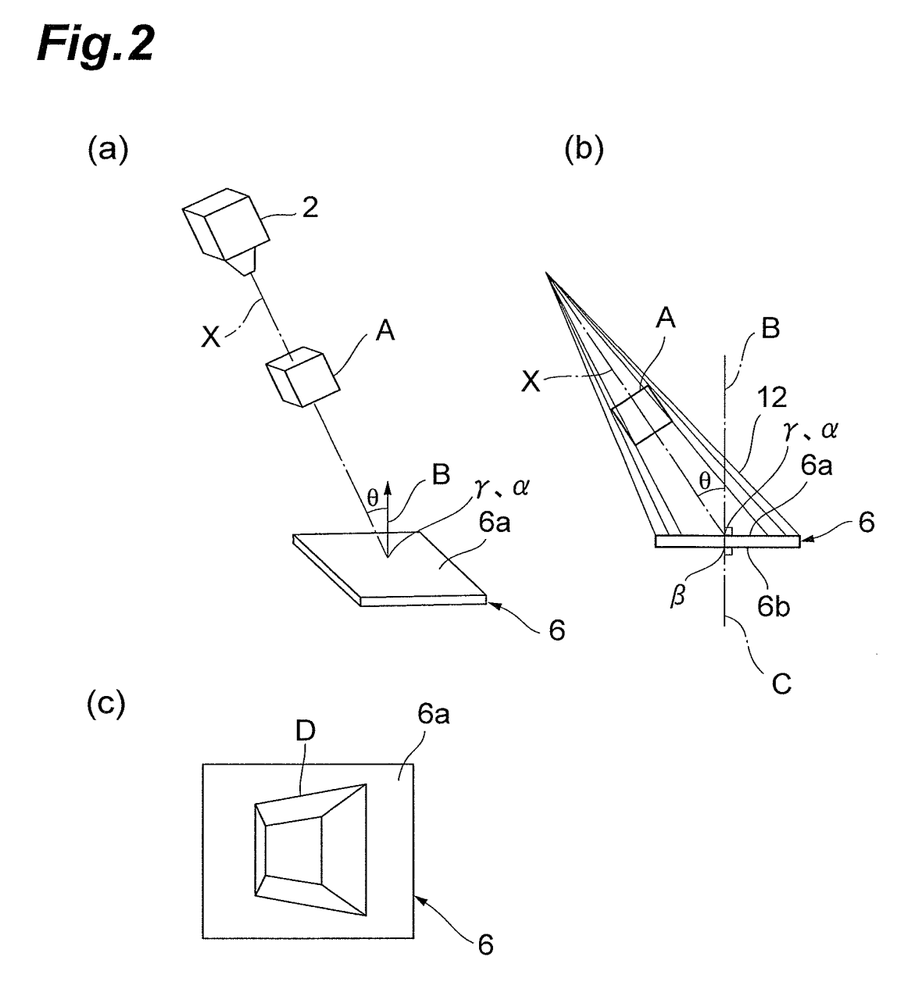
FIG. 2 is an explanatory drawing for explaining a perspective of a projection image in the radiation image acquisition device shown in FIG. 1.

FIG. 2(a) is a perspective view showing the positional relationship among the radiation source 2, object A, and wavelength conversion plate 6 in the radiation image acquisition device 1, FIG. 2(b) a front view showing the positional relationship among the radiation source 2, object A, and wavelength conversion plate 6, and FIG. 2(c) a plan view showing a projection image D of the object A projected on the wavelength conversion plate 6. FIG. 2 shows a situation in which the object A is of a 3D shape, for easier understanding. When the radiation source 2 is arranged at the position off the normal B to the entrance surface 6a and the optical axis X of the radiation makes the predetermined angle θ with respect to the normal B to the entrance surface 6a as shown in FIG. 2(a), a perspective is made in the projection image D onto the entrance surface 6a, as shown in FIG. 2(c). Since the front detector 3 and the back detector 4 take respective images of the projection image D from the directions of the normals B, C, respectively, no perspective is made in the taken images, which facilitates the operation between the two images in the image processing device 8. The perspective of the projection image D is corrected according to needs by the image processing device 8. Although FIG. 2(a) shows that the main body of the radiation source 2 is parallel to the optical axis X, for convenience' sake of explanation, the orientation of arrangement of the radiation source 2 can be optionally set according to the layout of the device.

In the radiation image acquisition device 1 of the present embodiment described above, the front detector 3 and the back detector 4 condense and image the respective scintillation light beams emitted from the entrance surface 6a and the back surface 6b of the wavelength conversion plate 6, thereby realizing the dual-energy imaging to acquire radiation images in different energy bands. In this configuration, the front detector 3 is arranged at the position apart from the wavelength conversion plate 6, without any detector interposed between the object A and the wavelength conversion plate 6. This configuration permits the device to avoid the incident that the imaging means affects the radiation transmitted by the object A. Therefore, the influence on the radiation transmitted by the object A is reduced and the radiation in a low energy band is suitably detected. In other words, no shadow of detector is cast on the radiation transmission images, so as to suppress generation of noise component and cause no attenuation of radiation due to the detector, thus suppressing reduction of signal components. As a result, it becomes feasible to make a difference between the low energy band and the high energy band in the dual-energy imaging larger and to exhibit a high energy resolution, allowing achievement of higher contrast. This advantage is prominently demonstrated, particularly, in the case where the object A is formed of silicon or an atom lighter in weight than silicon. Namely, even if the object A is formed of a lightweight atom, the radiation in the low energy band transmitted by the object A is converted into scintillation light, without being absorbed or attenuated, and this light is imaged by the front detector 3; therefore, the radiation image in the low energy band can be acquired with accuracy. In addition, the low-energy image and the high-energy image can be simultaneously acquired by a single imaging operation, so as to ensure simultaneity, reduce an exposure dose, and avoid pixel shifts (misregistration). The dual-energy imaging can be realized even by means of the single wavelength conversion plate 6. In addition, the front detector 3 and the back detector 4 condense the scintillation light beams emitted in the directions of the normals B, C, respectively, from the entrance surface 6a and the back surface 6b and thus both can acquire the radiation images without a perspective, which facilitates the operation between the images on the entrance surface 6a side and the back surface 6b side.

When white X-rays are used as the radiation, the low-energy image and the high-energy image can also be simultaneously acquired by a single imaging operation of white X-rays, so as to ensure simultaneity, reduce an exposure dose, and avoid pixel shifts (misregistration).

As the condensing lens unit 3a and the condensing lens unit 4a condense the light with focus on each of the entrance surface 6a and the back surface 6b of the wavelength conversion plate 6, bright radiation images can be acquired with good energy separation.

Since the front detector 3 directly condenses the scintillation light in the direction of the normal B to the entrance surface 6a and the front detector 3 is arranged off the optical axis X of the radiation source 2, the aforementioned operational effect is readily achieved and the front detector 3 is prevented from being exposed to the radiation, so as to suppress generation of noise inside the front detector 3.

Figure 3:
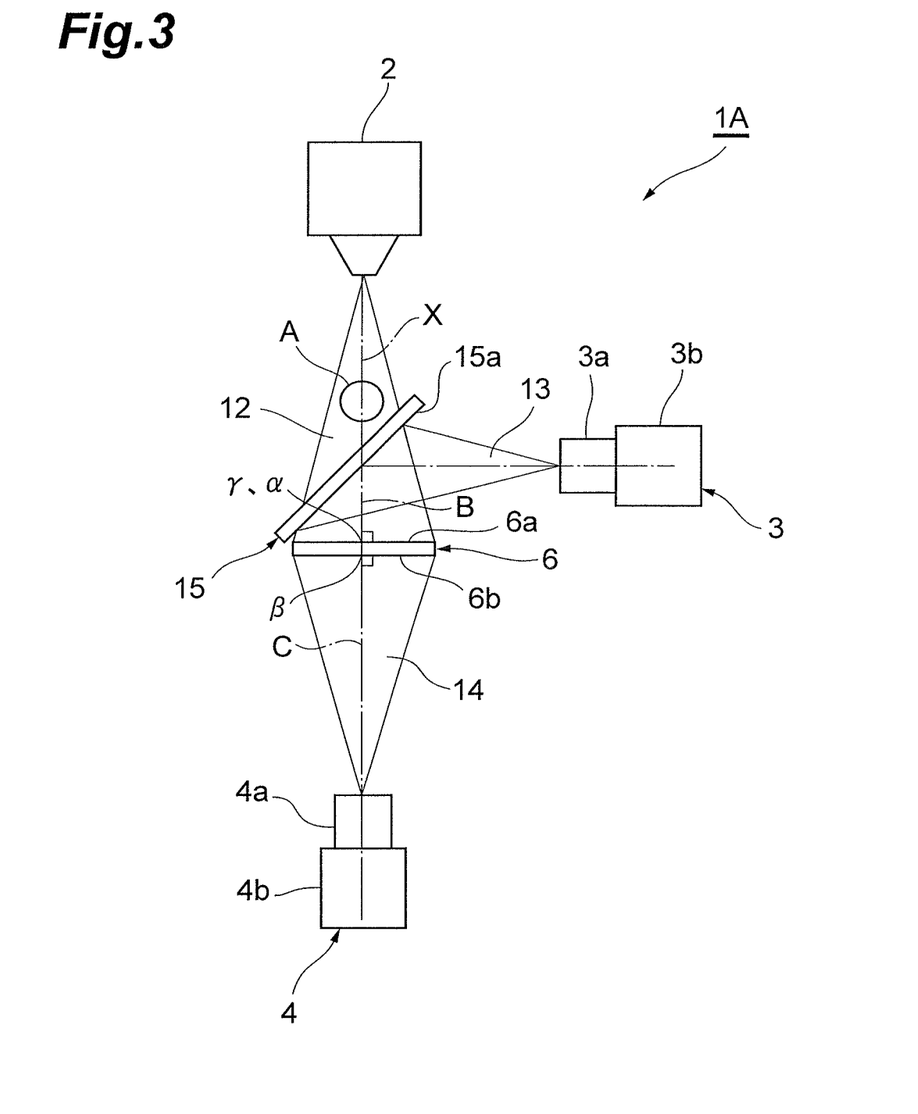
FIG. 3 is a front view of the radiation image acquisition device according to the second embodiment of the present invention.

FIG. 3 is a front view of the radiation image acquisition device according to the second embodiment. The radiation image acquisition device 1A shown in FIG. 3 is different from the radiation image acquisition device 1 shown in FIG. 1 in that the radiation source 2 is arranged on the normal B to the entrance surface 6a and in that the front detector 3 is arranged at a position off the normal B to the entrance surface 6a so as to condense the scintillation light via a reflecting mirror 15 arranged on the normal B (optical axis X) between the wavelength conversion plate 6 and the radiation source 2. FIG. 3 is depicted without illustration of the timing control unit 7, image processing device 8, and display device 9. FIGS. 5 to 8 are also depicted similarly without illustration of these components.

The configuration of the radiation image acquisition device 1A will be described more specifically. The radiation source 2 is arranged so that the optical axis X of the radiation is coincident with the normal B to the entrance surface 6a. The reflecting mirror 15 is arranged so that its reflective surface 15a makes a predetermined angle (e.g., 45°) with respect to the direction of the normal B so as to reflect the scintillation light emitted in the direction of the normal B from the entrance surface 6a, into a predetermined direction relative to the normal B. The reflecting mirror 15 to be used herein is, for example, an optical mirror that transmits the radiation. The front detector 3 is arranged so that an angle between the optical axis of the incorporated condensing lens unit 3a and the reflective surface 15a is equal to the angle between the normal B and the reflective surface 15a. This condensing lens unit 3a condenses the scintillation light emitted in the direction of the normal B from the entrance surface 6a and reflected into the predetermined direction relative to the normal B by the reflecting mirror 15, toward the imaging unit 3b.

As described above, the front detector 3 is arranged so as to be apart from the radiation emission region from the radiation source 2 (the region where the radiation beam 12 exists). This arrangement prevents the front detector 3 from being exposed to the radiation from the radiation source 2, and thus prevents a direct conversion signal of radiation from being produced inside the front detector 3 to generate noise. Furthermore, the optical path length from the entrance surface 6a of the wavelength conversion plate 6 to the front detector 3 may be set equal to the optical path length from the back surface 6b of the wavelength conversion plate 6 to the back detector 4.

Figure 4:
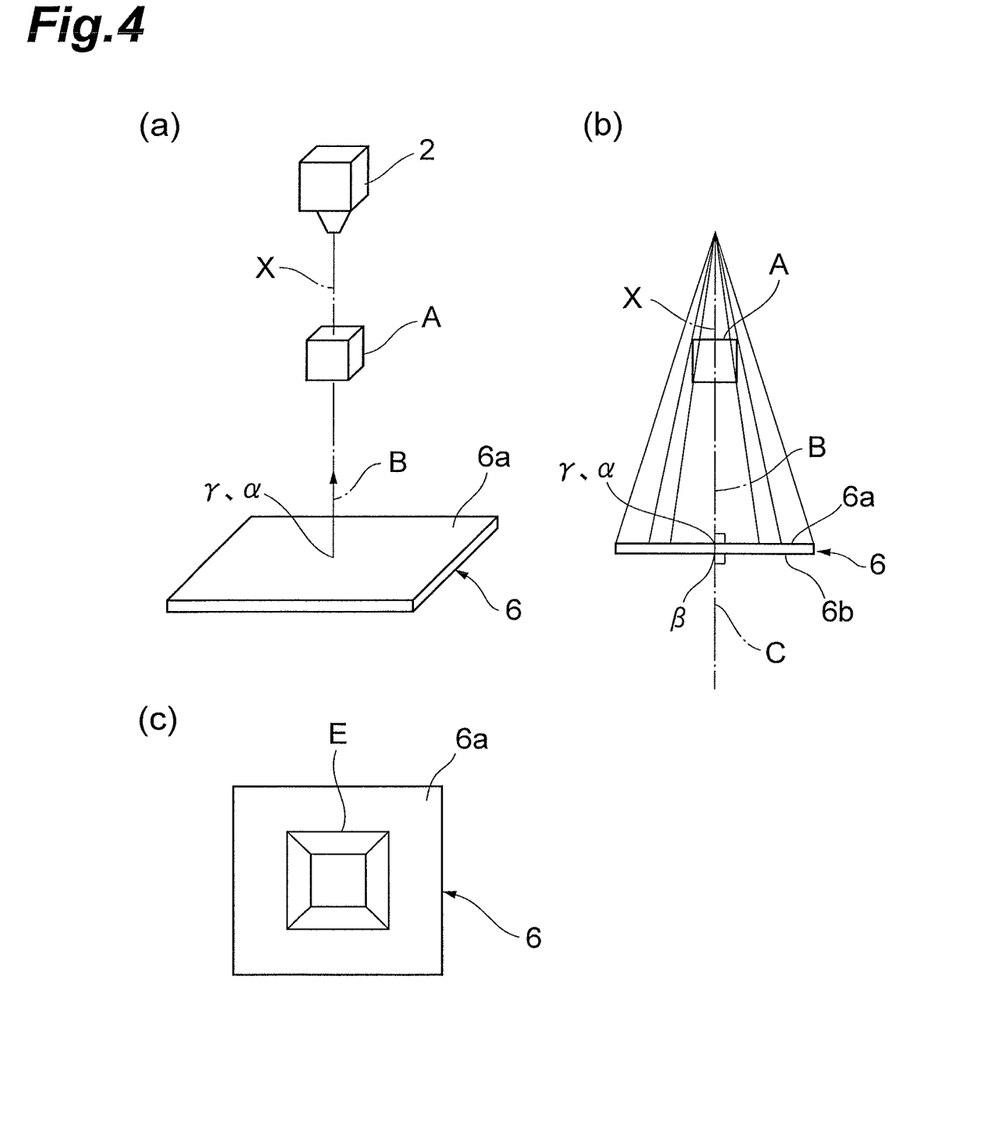
FIG. 4 is an explanatory drawing for explaining a projection image in the radiation image acquisition device shown in FIG. 3.

FIG. 4(a) is a perspective view showing the positional relationship among the radiation source 2, object A, and wavelength conversion plate 6 in the radiation image acquisition device 1A, FIG. 4(b) a front view showing the positional relationship among the radiation source 2, object A, and wavelength conversion plate 6, and FIG. 4(c) a plan view showing a projection image E of the object A projected on the wavelength conversion plate 6. FIG. 4 shows a situation in which the object A is of a 3D shape, for easier understanding. When the radiation source 2 is arranged on the normal B to the entrance surface 6a and the optical axis X of the radiation is coincident with the normal B to the entrance surface 6a as shown in FIG. 4(a), no perspective is made in the projection image E onto the entrance surface 6a, as shown in FIG. 4(c). Since the front detector 3 takes an image of the projection image E from the direction of the normal B via the reflecting mirror 15 and the back detector 4 takes an image of the projection image E from the direction of the normal C, no perspective is made in the taken images, which facilitates the operation between the two images in the image processing device 8. Since there is no perspective in the projection image E, no perspective correction is needed in the image processing device 8. Since the reflecting mirror 15 is arranged on the optical axis X of the radiation source 2 in the radiation image acquisition device 1A, the reflecting mirror 15 absorbs some radiation.

The radiation image acquisition device 1A achieves the same operational effect as the radiation image acquisition device 1 does. Since the radiation source 2 is arranged on the normal B to the entrance surface 6a, no perspective is made in the projection image E onto the wavelength conversion plate 6 and thus there is no need for an operation for correction for a perspective of the projection image E. Furthermore, the front detector 3 is prevented from being exposed to the radiation, which prevents generation of noise inside the front detector 3.

Figure 5:
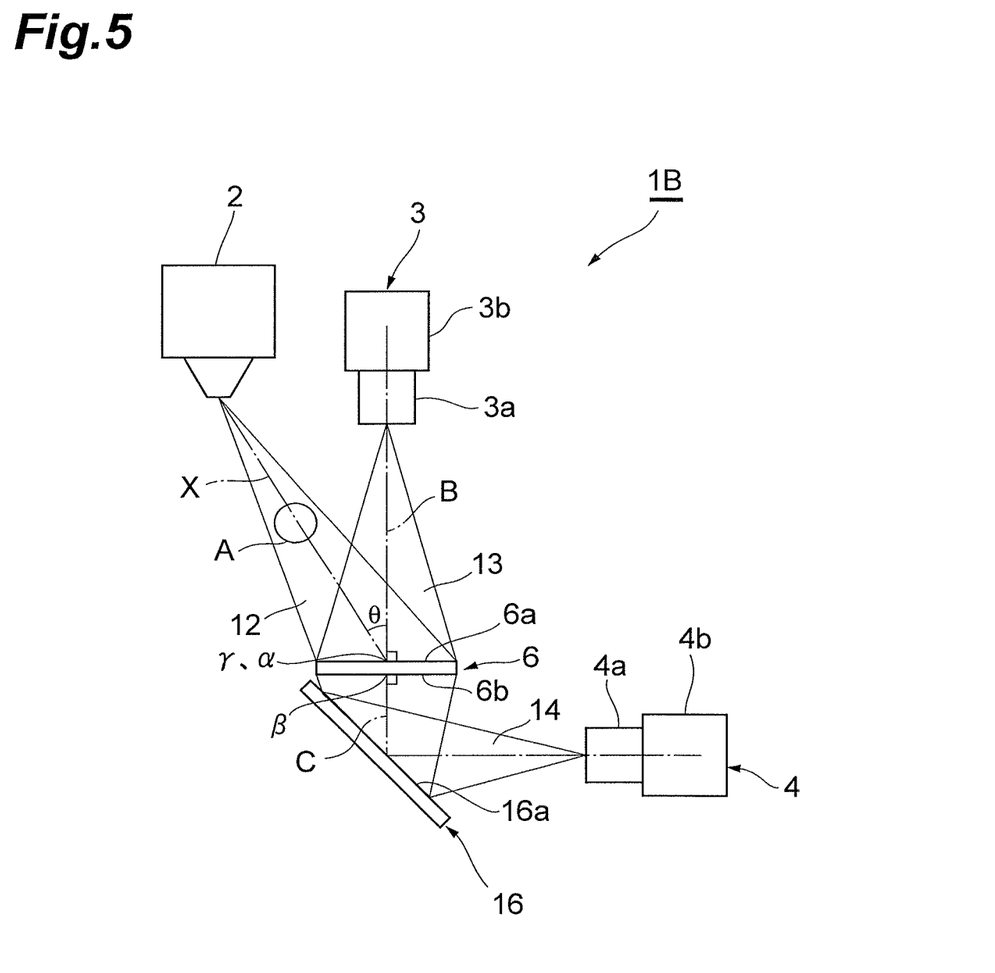
FIG. 5 is a front view of the radiation image acquisition device according to the third embodiment of the present invention.

FIG. 5 is a front view of the radiation image acquisition device according to the third embodiment. The radiation image acquisition device 1B shown in FIG. 5 is different from the radiation image acquisition device 1 of the first embodiment shown in FIG. 1 in that the back detector 4 is arranged at a position off the normal C to the back surface 6b so as to condense the scintillation light via a reflecting mirror 16 arranged on the normal C. More specifically, the reflecting mirror 16 is arranged so that its reflective surface 16a makes a predetermined angle (e.g., 45°) with respect to the direction of the normal C and thus it reflects the scintillation light emitted in the direction of the normal C from the back surface 6b, into a predetermined direction with respect to the normal C. The reflecting mirror 16 to be used herein is, for example, an optical mirror or a prism. The back detector 4 is arranged so that an angle between the optical axis of the incorporated condensing lens unit 4a and the reflective surface 16a is equal to the angle between the normal C and the reflective surface 16a. This condensing lens unit 4a condenses the scintillation light emitted in the direction of the normal C from the back surface 6b and reflected in the predetermined direction relative to the normal C by the reflecting mirror 16, toward the imaging unit 4b.

As described above, the back detector 4 is arranged so as to be apart from the radiation emission region from the radiation source 2 (the region where the radiation beam 12 exists). This arrangement prevents the back detector 4 from being exposed to the radiation from the radiation source 2, and thus prevents a direct conversion signal of radiation from being produced inside the back detector 4 to generate noise. Furthermore, the optical path length from the entrance surface 6a of the wavelength conversion plate 6 to the front detector 3 may be set equal to the optical path length from the back surface 6b of the wavelength conversion plate 6 to the back detector 4.

The radiation image acquisition device 1B achieves the same operational effect as the radiation image acquisition devices 1 and 1A do. In addition, the back detector 4 is prevented from being exposed to the radiation, which prevents generation of noise inside the back detector 4. Furthermore, the optical path lengths from the wavelength conversion plate 6 to the front detector 3 and the back detector 4 are allowed to adjust, which facilitates position alignment of the first and second imaging means. As a consequence of this, it becomes easier to match the imaging conditions of the first and second imaging means (e.g., simultaneity of imaging times and identity of imaging positions).

Figure 6:
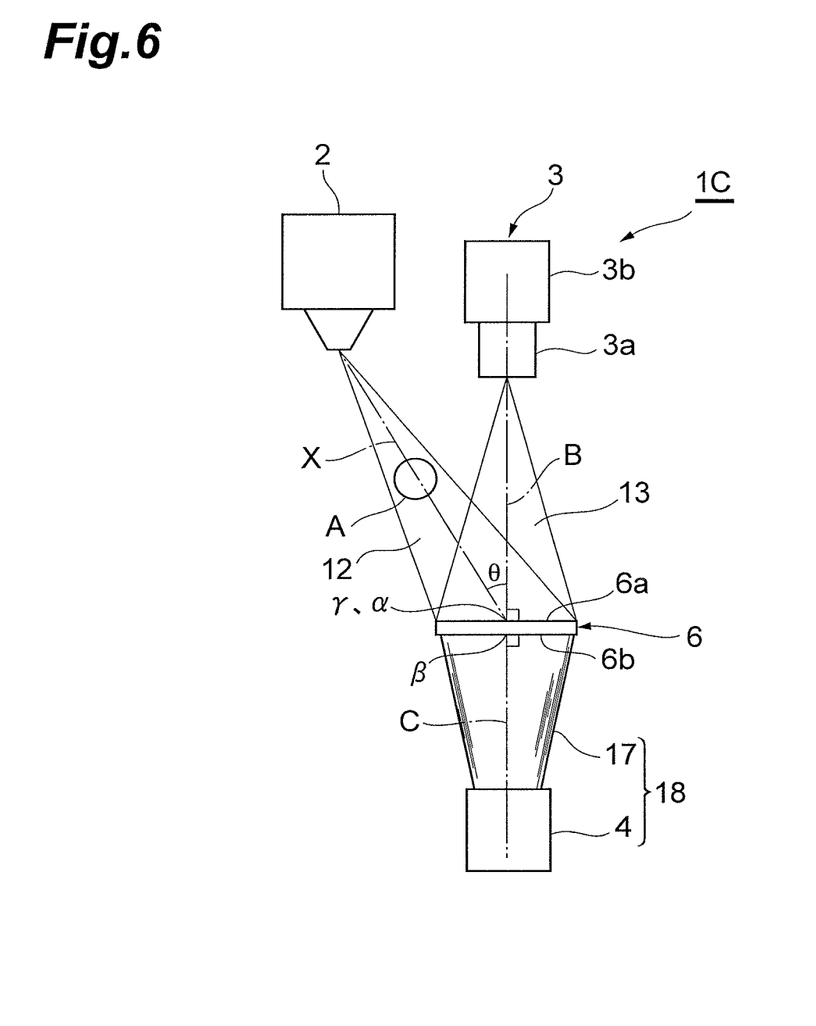
FIG. 6 is a front view of the radiation image acquisition device according to the fourth embodiment of the present invention.

FIG. 6 is a front view of the radiation image acquisition device according to the fourth embodiment. The radiation image acquisition device 1C shown in FIG. 6 is different from the radiation image acquisition device 1 of the first embodiment shown in FIG. 1 in that a tapered fiber 17 is arranged so as to face the back surface 6b between the back surface 6b and the back detector 4. More specifically, the tapered fiber 17 is arranged so that its axis is coincident with the normal C to the back surface 6b, so as to guide the scintillation light emitted in the direction of the normal C from the back surface 6b, to the condensing lens unit of the back detector 4. This tapered fiber 17 and the back detector 4 constitute a fiber coupling detector 18.

The radiation image acquisition device 1C achieves the same operational effect as the radiation image acquisition devices 1, 1A, and 1B do. The tapered fiber 17 condenses the scintillation light on the back surface 6b side at a high light condensing efficiency. An ordinary fluorescent image tends to become dark on the back surface 6b side of the wavelength conversion plate 6, but a loss in the optical system can be reduced by adopting the fiber coupling detector 18. Furthermore, the tapered fiber 17 blocks the radiation from the radiation source 2, so as to prevent exposure of the back detector 4 thereto.

Figure 7:
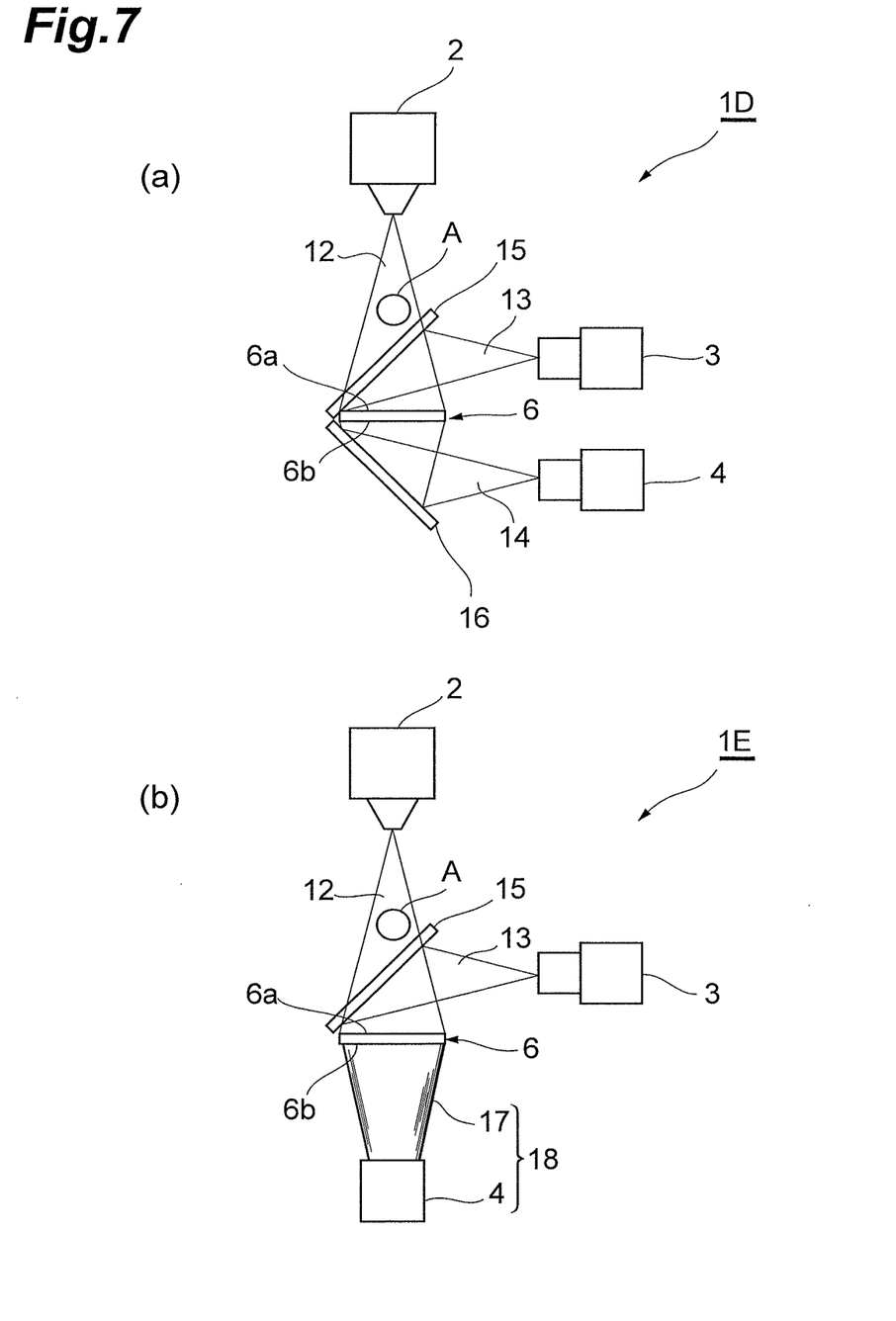

The above described the embodiments of the present invention but the present invention is by no means intended to be limited to the above embodiments. For example, various modifications as shown in FIG. 7 may be adopted in the configuration wherein the radiation source 2 is arranged on the normal B to the entrance surface 6a. Specifically, as shown in FIG. 7(a), the radiation image acquisition device 1D may be so configured that the reflecting mirror 15 is arranged on the entrance surface 6a side and that the reflecting mirror 16 is arranged on the back surface 6b side. Furthermore, as shown in FIG. 7(b), the radiation image acquisition device 1E may be so configured that the reflecting mirror 15 is arranged on the entrance surface 6a side and that the fiber coupling detector 18 is arranged on the back surface 6b side.

Figure 8:
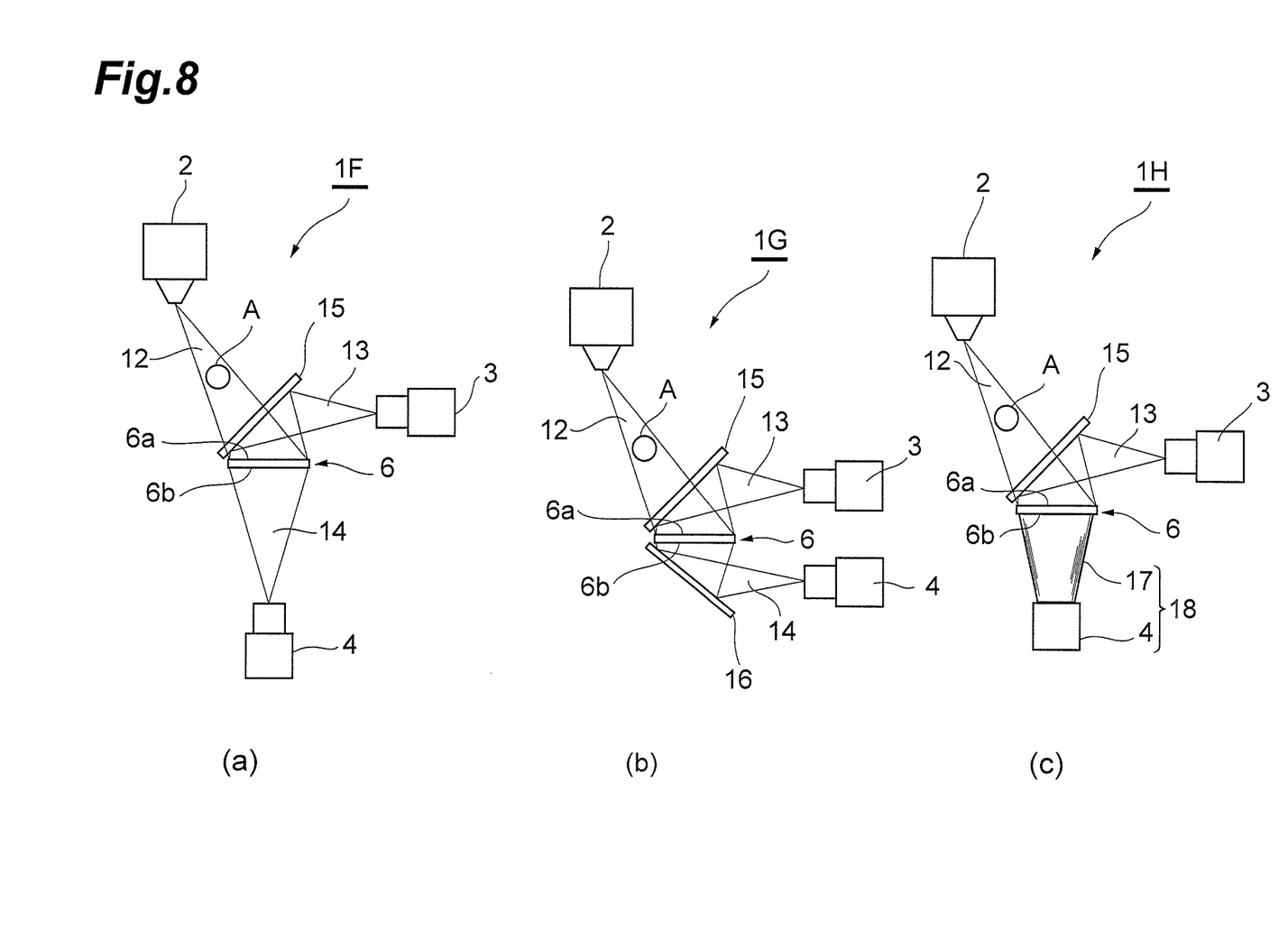
FIG. 8(a) to (c) is front views of the radiation image acquisition devices which are modification examples of the present invention.

Furthermore, various modifications as shown in FIG. 8 can also be adopted in the configuration wherein the radiation source 2 is arranged at the position off the normal B to the entrance surface 6a. Specifically, as shown in FIG. 8(a), the radiation image acquisition device 1F may be so configured that the reflecting mirror 15 is arranged on the entrance surface 6a side and that the back detector 4 is arranged on the normal C to the back surface 6b. Moreover, as shown in FIG. 8(b), the radiation image acquisition device 1G may be so configured that the reflecting mirror 15 is arranged on the entrance surface 6a side and that the reflecting mirror 16 is arranged on the back surface 6b side. Furthermore, as shown in FIG. 8(c), the radiation image acquisition device 1H may be so configured that the reflecting mirror 15 is arranged on the entrance surface 6a side and that the fiber coupling detector 18 is arranged on the back surface 6b side.

The above embodiments, in the cases using the reflecting mirror 15 or 16, described the examples wherein the reflecting mirror 15, 16 was arranged at the angle of 45° with respect to the normal B, C and wherein the optical axis of the condensing lens unit was perpendicular to the normal B, C, but, without having to be limited to this arrangement, the angle of the reflecting mirror 15, 16 and the arrangement of the front detector 3 and the back detector 4 may be optionally modified according to the layout in the device.

The above embodiments described the examples wherein the arbitrary point γ and the arbitrary point α coincided on the entrance surface 6a, but they may be located at different positions on the entrance surface 6a. In this case, the radiation source 2 may be arranged so that the optical axis X is perpendicular to the entrance surface 6a and the front detector 3 may be arranged so that the optical axis of the condensing lens unit 3a is perpendicular to the entrance surface 6a.

Namely, the optical axis X of the radiation source 2 and the optical axis of the condensing lens unit 3a are parallel to each other and a separation distance between these optical axes becomes equal to a separation distance between the point γ and the point α. In this configuration, the front detector 3 can condense and image the scintillation light emitted in the direction of the normal to the entrance surface 6a.

The above embodiments used the lens coupling type detectors as detectors, but the condensing lens unit and the imaging unit may be provided as separate members.

An effective application is such that the object A is a semiconductor device and the radiation image acquisition device of the above embodiment is applied to a semiconductor failure inspection device an inspection target of which is the semiconductor device. In this case, the radiation transmitted by the semiconductor device as the inspection target is not cut by the imaging unit (imaging device for acquisition of image) and thus a failure or the like of the semiconductor device can be detected with accuracy.

INDUSTRIAL APPLICABILITY

The one aspect of the present invention enables the acquisition of radiation images in different energy bands and the reduction of the influence on the radiation transmitted by the object.

REFERENCE SIGNS LIST 1, 1A-1H radiation image acquisition devices; 2 radiation source; 3 front observation photodetector (first imaging means); 3a condensing lens unit; 3b imaging unit; 4 back observation photodetector (second imaging means); 4a condensing lens unit; 4b imaging unit; 6 wavelength conversion plate (wavelength conversion member); 6a entrance surface; 6b back surface (opposite surface); 15 reflecting mirror; 16 reflecting mirror; 17 tapered fiber; A object; B normal to entrance surface; C normal to back surface.

The invention claimed is:

1. A radiation image acquisition device comprising:
a radiation source configured to emit radiation;
a wavelength conversion member of a flat plate shape configured to generate scintillation light according to incidence of the radiation emitted from the radiation source and transmitted by an object;
first imaging means configured to condense and image the scintillation light emitted from an entrance surface for the radiation in the wavelength conversion member in a direction of a normal to the entrance surface; and
second imaging means configured to condense and image the scintillation light emitted from a surface opposite to the entrance surface in the wavelength conversion member in a direction of a normal to the opposite surface,
wherein each of the first imaging means and the second imaging means has:
a condensing lens unit configured to condense the scintillation light emitted from the wavelength conversion member; and
an imaging unit configured to image the scintillation light thus condensed,
wherein the condensing lens unit of the first imaging means is configured to focus on the entrance surface and condense the scintillation light emitted in the direction of the normal from the entrance surface toward the imaging unit, and
wherein the condensing lens unit of the second imaging means is configured to focus on the opposite surface and condense the scintillation light emitted in the direction of the normal from the opposite surface toward the imaging unit.

2. The radiation image acquisition device according to claim 1,
wherein an optical axis of the condensing lens unit of the first imaging means is perpendicular to the entrance surface.

3. The radiation image acquisition device according to claim 1,
wherein the first imaging means is arranged so that a vertical line descending from a central point of the condensing lens unit of the first imaging means to the entrance surface is within the range of the entrance surface.

4. The radiation image acquisition device according to claim 1,
wherein an optical axis of the condensing lens unit of the second imaging means is perpendicular to the opposite surface.

5. The radiation image acquisition device according to claim 1,
wherein the radiation source is arranged so that an angle between an optical axis of the radiation source and the entrance surface is larger than 0° and smaller than 90°, and wherein the first imaging means is arranged on the normal to the entrance surface.

6. The radiation image acquisition device according to claim 1,
wherein the radiation source is arranged on the normal to the entrance surface, and
wherein the first imaging means is arranged at a position off the normal to the entrance surface so as to condense the scintillation light via a reflecting mirror arranged between the wavelength conversion member and the radiation source.

7. The radiation image acquisition device according to claim 6,
wherein the reflecting mirror is arranged so that a reflecting surface thereof makes a predetermined angle with respect to the direction of the normal to the entrance surface, and reflects the scintillation light emitted in the direction of the normal from the entrance surface in a predetermined direction with respect to the direction of the normal to the entrance surface.

8. The radiation image acquisition device according to claim 6,
wherein the first imaging means is arranged so that an angle between an optical axis of a condensing lens unit of the first imaging means and a reflecting surface of the reflecting mirror is equal to an angle between the normal to the entrance surface and the reflecting surface.

9. The radiation image acquisition device according to claim 1,
wherein the second imaging means is arranged at a position off the normal to the opposite surface so as to condense the scintillation light via a reflecting mirror arranged on the normal to the opposite surface.

10. The radiation image acquisition device according to claim 9,
wherein the reflecting mirror is arranged so that a reflecting surface thereof makes a predetermined angle with respect to the direction of the normal to the opposite surface, and reflects the scintillation light emitted in the direction of the normal to the opposite surface from the opposite surface in a predetermined direction with respect to the direction of the normal to the opposite surface.

11. The radiation image acquisition device according to claim 9,
wherein the second imaging means is arranged so that an angle between an optical axis of a condensing lens unit of the second imaging means and a reflecting surface of the reflecting mirror is equal to an angle between the normal to the opposite surface and the reflecting surface.

12. The radiation image acquisition device according to claim 1,
wherein a tapered fiber is arranged between the opposite surface of the wavelength conversion member and the second imaging means so as to face the opposite surface.

13. The radiation image acquisition device according to claim 12,
wherein the tapered fiber is arranged so that an axis thereof is coincident with the normal to the opposite surface, and guides the scintillation light emitted in the direction of the normal to the opposite surface from the opposite surface to a condensing lens unit of the second imaging means.

14. The radiation image acquisition device according to claim 1,
wherein a light receiving surface of the first imaging means is parallel to the entrance surface.

15. The radiation image acquisition device according to claim 1,
wherein a light receiving surface of the second imaging means is parallel to the opposite surface.

16. The radiation image acquisition device according to claim 1,
wherein the first imaging means faces the entrance surface and is arranged on the normal to the entrance surface.

17. The radiation image acquisition device according to claim 1,
wherein the second imaging means faces the opposite surface and is arranged on the normal to the opposite surface.

18. The radiation image acquisition device according to claim 1,
wherein an optical path length from the entrance surface to the first imaging means is equal to an optical path length from the opposite surface to the second imaging means.

19. The radiation image acquisition device according to claim 1,
wherein the first and second imaging means are configured so as to perform imaging simultaneously.

20. The radiation image acquisition device according to claim 1,
wherein the object is a semiconductor device,
said radiation image acquisition device being applied to a semiconductor failure inspection device an inspection target of which is the semiconductor device.

21. The radiation image acquisition device according to claim 1,
wherein the object is an electronic component.

* * * * *